US007025754B2

(12) United States Patent
Proicou et al.

(10) Patent No.: US 7,025,754 B2
(45) Date of Patent: Apr. 11, 2006

(54) DRUG CONTAINMENT SYSTEM

(75) Inventors: George C. Proicou, Gahanna, OH (US); Richard D. Peters, Gahanna, OH (US); David Rust Busick, Lewis Center, OH (US); Theodore Robert Adams, Dublin, OH (US)

(73) Assignee: Ventaira Pharmaceuticals, Inc., Columbus, OH (US)

( * ) Notice: Subject to any disclaimer, the term of this patent is extended or adjusted under 35 U.S.C. 154(b) by 154 days.

(21) Appl. No.: 10/187,477

(22) Filed: Jul. 1, 2002

(65) Prior Publication Data

US 2004/0001655 A1 Jan. 1, 2004

(51) Int. Cl.
*A61M 19/00* (2006.01)

(52) U.S. Cl. ...................... 604/408; 604/403; 604/415; 604/905; 128/DIG. 24

(58) Field of Classification Search ................ 604/403, 604/407–416, 262, 288.02, 905, 4.01, 6.154, 604/500, 518, 520, 522, 19, 82, 83, 906, 604/86–90, 200–206, 93.01, 257, 261–62, 604/288.01; 128/DIG. 24; 383/9, 904, 906; 600/573, 580, 576–579

See application file for complete search history.

(56) References Cited

U.S. PATENT DOCUMENTS

| | | | | | |
|---|---|---|---|---|---|
| 2,072,225 | A | * | 3/1937 | Slater | 383/41 |
| 2,116,009 | A | * | 5/1938 | Brown | 604/80 |
| 2,848,995 | A | * | 8/1958 | Ryan | 604/406 |
| 3,064,652 | A | * | 11/1962 | Corcoran et al. | 604/111 |
| 3,325,031 | A | * | 6/1967 | Singier | 215/247 |
| 3,498,295 | A | * | 3/1970 | Tamagni et al. | 604/415 |
| 3,554,256 | A | * | 1/1971 | Anderson | 604/408 |
| 3,915,212 | A | * | 10/1975 | Bujan et al. | 604/408 |
| 3,930,500 | A | | 1/1976 | Möhrke et al. | |
| 3,938,513 | A | | 2/1976 | Hargest | |
| 4,176,507 | A | | 12/1979 | Mancini | |
| 4,257,535 | A | * | 3/1981 | Mellett | 222/92 |
| 4,268,531 | A | | 5/1981 | Whiting, Jr. | |
| 4,303,067 | A | * | 12/1981 | Connolly et al. | 604/408 |
| 4,439,192 | A | * | 3/1984 | Leurink | 604/408 |
| 4,484,916 | A | * | 11/1984 | McPhee | 604/256 |
| 4,488,877 | A | | 12/1984 | Klein et al. | |
| 4,516,977 | A | * | 5/1985 | Herbert | 604/415 |
| 4,596,573 | A | * | 6/1986 | Donnan et al. | 604/415 |
| 4,596,575 | A | | 6/1986 | Rosenberg et al. | |

(Continued)

FOREIGN PATENT DOCUMENTS

WO 99/02119 1/1999

(Continued)

OTHER PUBLICATIONS

Brochure by Speedline Technologies entitled "*Specialty Coating Systems. Parylene: A Biostable Biocompatible Coating for Medical Devices*" (2000).

(Continued)

*Primary Examiner*—Patricia Bianco
(74) *Attorney, Agent, or Firm*—Gibbons, Del Deo, Dolan, Griffinger and Vecchione

(57) ABSTRACT

A container closure device for facilitating withdrawal of a liquid from a collapsible sealed packet is disclosed. The device includes a needle guide and a septum retainer wherein the needle guide is fixable to an outer face of the packet and the septum retainer is fixable to an inner face of the packet in alignment with the needle guide. The needle guide includes a tube for receiving a needle and insures proper alignment of the needle. The septum retainer includes a septum chamber having a septum disposed therein.

26 Claims, 3 Drawing Sheets

U.S. PATENT DOCUMENTS 4,632,673 A * 12/1986 Tiitola et al. ............... 604/415
4,636,412 A * 1/1987 Field .......................... 604/408
4,756,974 A 7/1988 Romberg
5,129,894 A * 7/1992 Sommermeyer et al. .... 604/408
5,259,844 A * 11/1993 Bilstad et al. .............. 604/408
5,303,838 A * 4/1994 Luch et al. ................. 220/270
5,332,095 A * 7/1994 Wu ......................... 206/524.8
5,405,333 A * 4/1995 Richmond .................. 604/257
5,653,757 A * 8/1997 Petrick ....................... 128/898
5,681,666 A 10/1997 Treger et al.
5,693,035 A * 12/1997 Leise et al. ................. 604/333
5,718,334 A 2/1998 Demel
5,755,081 A 5/1998 Rivett et al.
5,769,255 A 6/1998 Ohmi et al.
5,785,688 A 7/1998 Joshi et al.
5,799,693 A 9/1998 Strong
5,819,986 A 10/1998 Last et al.
5,826,755 A 10/1998 Burd
5,836,484 A 11/1998 Gerber
5,853,247 A * 12/1998 Shroyer ....................... 383/95
5,919,182 A 7/1999 Avallone
6,022,145 A 2/2000 Searfoss
6,079,449 A 6/2000 Gerber
6,123,068 A 9/2000 Lloyd et al.
6,126,045 A 10/2000 Last
6,250,508 B1 * 6/2001 Geser et al. ............. 222/189.1
6,302,331 B1 10/2001 Dvorsky et al.
6,332,552 B1 12/2001 Iwasaki et al.
6,334,556 B1 1/2002 Bougamont et al.
6,354,516 B1 3/2002 Patel et al.
6,375,022 B1 * 4/2002 Zurcher et al. ............. 215/247
6,394,993 B1 * 5/2002 Chang et al. ............... 604/415
6,426,046 B1 * 7/2002 Cassells et al. ............... 422/99
6,582,415 B1 * 6/2003 Fowles et al. .............. 604/413
2002/0035820 A1 3/2002 Farris
2002/0123736 A1 * 9/2002 Fowles et al. .............. 604/413

FOREIGN PATENT DOCUMENTS

WO 00/49988 8/2000

OTHER PUBLICATIONS

Website by Speedline Technologies, regarding "*Parylene Coating*" (Jun. 5, 2002).
Brochure by Honeywell entitled "A Clear Choice for Barrier Protection. ACLAR Barrier Films" (date unknown).

* cited by examiner

DRUG CONTAINMENT SYSTEM

BACKGROUND OF THE INVENTION

The present invention relates to a container closure device for facilitating withdrawal of a liquid from a collapsible sealed packet and a liquid containment system utilizing such a device, wherein the device comprises a needle guide and a septum retainer.

U.S. Pat. No. 6,250,508 discloses an apparatus for withdrawing a liquid from a closed container wherein the closed container is provided with an open-pore porous storage medium in the form of an integral body. The storage medium touches the liquid at least at times and is located near the end of the withdrawal connection portion. The container allows for withdrawal of liquid from the closed container when the container is in any position and provides almost complete withdrawal of liquid from the closed container. The container can be used for withdrawing a liquid medicament to be used in an atomizer to produce an inhalable aerosol.

International Patent Application WO 00/49988 to Kladders et al. discloses a cartridge for a liquid which can be used in an atomizer for generating an aerosol which can be inhaled for the treatment of illnesses The cartridge comprises a collapsible bag containing the liquid, a dimensionally stable container, and a stiff metal shell. The cartridge is detachably connected to a withdrawing device.

The present invention provides a compact and efficient device of withdrawing liquid from a collapsible sealed packet and a liquid containment system utilizing such a device for connection to a liquid delivery device, in particular, for connection to an aerosol delivery device useful to produce and deliver aerosols of therapeutic medicaments.

SUMMARY OF THE INVENTION

In accordance with one aspect of the present invention, a container closure device for facilitating withdrawal of a liquid from a collapsible sealed packet is disclosed that includes a needle guide and a septum retainer. The container closure device is designed so as to maintain the integrity of the sealed container and the contents enclosed therein. The collapsible sealed packet remains intact until pierced to withdraw the packet contents. The needle guide is fixable to an outer face of the packet and the septum retainer is fixable to an inner face of the packet in alignment with the needle guide. The needle guide includes a tube for receiving a needle and insuring proper alignment of the needle and the septum retainer comprises a septum chamber having a septum disposed therein.

In accordance with a particular embodiment of the invention, the septum retainer further comprises a cavity which receives the tip of an inserted needle and prevents the tip from contacting the adjacent face of the packet. The septum retainer may also comprise a septum chamber having a septum barrier wherein the septum is retained in isolation from the liquid contents of the packet such that the septum is not exposed to the liquid contents of the packet until ready for use.

In accordance with another aspect of the invention, the needle guide and septum container include complementary contours which facilitate alignment of the septum retainer with the needle guide when the septum retainer is placed on the inner face of the packet and the needle guide is placed on the outer face of the packet. In operation, fluid communication between a fluid delivery device and the collapsible sealed packet is established by inserting a needle through the tube of the needle guide piercing the packet laminate, through the septum and piercing a septum barrier to establish fluid communication between the packet contents and the liquid delivery device. When the hollow needle is thus inserted, the lower end of the needle resides in the cavity of the septum retainer without contacting the adjacent face of the packet. In accordance with particular aspects of the present invention, the septum retainer comprises a raised portion which prevents collapse of the packet around the cavity of the septum retainer as the liquid is withdrawn from the packet. In still more specific embodiments of the present invention, the septum retainer further comprises a plurality of channels extending radially from the cavity of the retainer which allow for continued liquid withdrawal as the packet collapses.

In another embodiment of the invention, the septum retainer is secured to the inner face of the packet using a method which minimizes the potential for contamination of the liquid contents of the sealed packet. In accordance with this embodiment, the septum retainer and inner face of the packet are constructed of materials capable of forming a heat seal or of being ultra-sonically welded. In accordance with one embodiment of the invention, the septum retainer comprises a polyethylene terephthalate (PET) and the inner face of the packet also comprises a polyethylene terephthalate (PET). The septum retainer and inner face are capable of forming a seal to secure the septum retainer to the inner face while minimizing the potential for contamination.

In accordance with certain aspects of the invention, the needle guide is secured to the outer face of the packet using either an adhesive seal or a heat seal. In a particular embodiment of the invention, a polycarbonate needle guide is secured to a polyethylene terephthalate (PET) outer face of the packet using a liquid UV cured adhesive.

In still another embodiment of the invention, the liquid containment system comprises a means for attaching the container packet to a liquid delivery device in such a way that the packet is securely held and can be pierced with a needle without applying pressure to the contents in the package. In accordance with one example of this embodiment of the invention, the needle guide is provided with a radially outwardly extending annular flange which engages a two-prong fork on the fluid delivery device which brings the sealed packet into alignment with a needle on the liquid delivery device. Once the liquid containing packet is properly aligned with the needle, the needle passes through the needle guide, pierces the packet extending through the septum, and piercing the septum barrier to reside in the septum cavity to establish fluid communication between the liquid delivery device and the contents of the packet.

In another embodiment of the present invention, a liquid containment system comprising a collapsible sealed packet, a needle guide and a septum retainer is disclosed. The collapsible sealed packet comprises first and second sheets superimposed and sealed together at their periphery to form a packet defining an interior for containing the liquid. The needle guide is secured to an outer face of the packet and the septum retainer is secured to an inner face of the packet aligned with the needle guide. The sealed packet provides a substantially airtight, sealed, integral unit for maintaining the enclosed contents for an extended period of time without significant changes in concentration, activity, etc. of the enclosed liquid. The collapsible sealed packed may be used to store and deliver a variety of liquids including solutions, suspensions or emulsions. In accordance with particular aspects of the invention, the liquid is a medicament dissolved in a solvent useful in producing an aerosol for inhalation therapy.

DETAILED DESCRIPTION OF THE INVENTION

Figure 1:
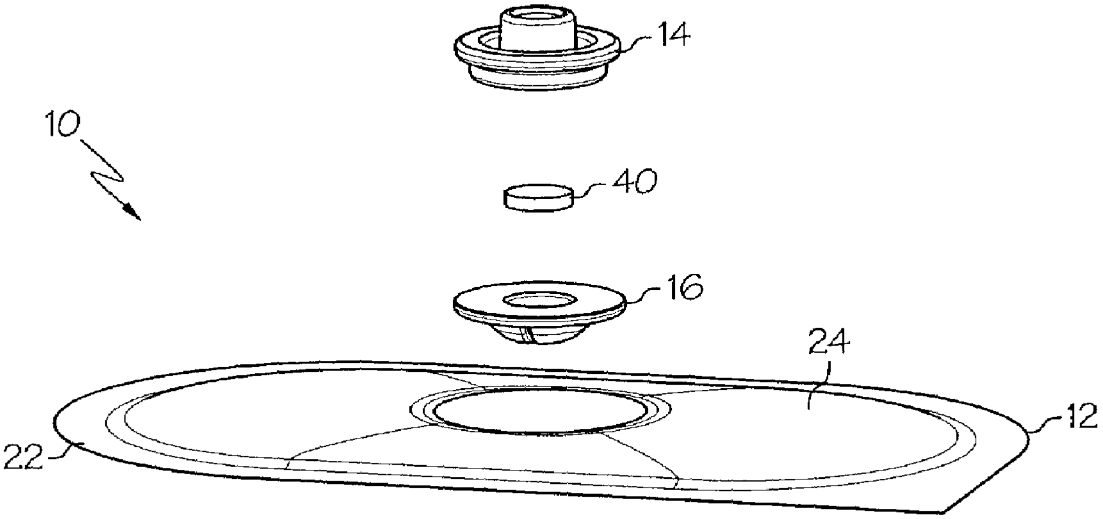
FIG. 1 is an exploded view of a liquid containment system in accordance with one embodiment of the present invention showing the individual components of the system.
Figure 2:
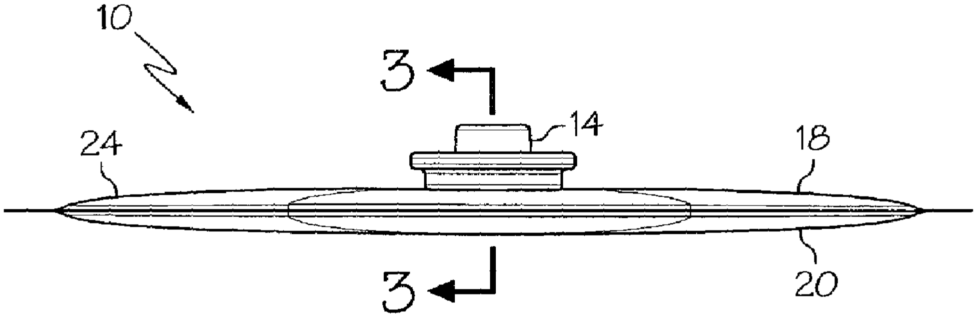
FIG. 2 is a side view of the liquid containment system of FIG. 1.
Figure 3:
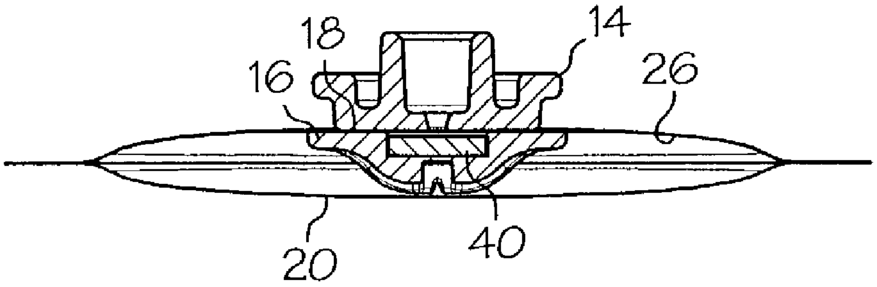
FIG. 3 is a cross-section along the line 2—2 of FIG. 2.

As depicted in FIGS. 1–3, in accordance with one embodiment of the present invention, a liquid containment system, generally shown at 10, includes a collapsible sealed packet 12, a needle guide 14 and a septum retainer 16.

The collapsible sealed packet 12 comprises first and second flexible sheets 18, 20 superimposed and sealed together at their periphery 22 thereby forming an interior for containing the liquid. Each of the superimposed sheets is preferably a multilayer film comprising a barrier layer and an inner heat sealable ply. Alternatively the multilayer film may comprise an exterior surface ply, a barrier layer and an inner heat sealable ply. Packets may be formed by bringing the inner plies of superimposed films into contact with one another and then applying sufficient heat and pressure to all but one of the open edges thereof, filling the packet with a liquid via the open edge, and then sealing closed, either by heat or by ultra-sonic welding, the remaining open edge to enclose the liquid in the packet 12. As used herein, the term "seal", or "heat-seal" refers to the union of two materials, typically films, by bringing the materials into contact with one another and then by ultra-sonic welding or by applying sufficient heat and pressure to the contacting regions to secure the materials together. In accordance with the formation of the packet 12, the heat-seal is continuous and encloses the liquid between the two films, and may be formed by a mechanism that includes a heated element which is pressed on to the contacting regions of the films from one side of one of the films and typically presses the films against a non-heated backing element so that the films are pressed between the heated element and the backing element for a period of time sufficient to effect a heat-seal.

In accordance with one embodiment of the present invention, the outer surface ply of the film is a polyethylene terephthalate (PET), the barrier layer is a metallic foil or high barrier polymer and the inner heat sealable ply is a polyethylene terephthalate (PET) or polyacrylonitrile ("A/MA/B") (also referred to as "PAN"). The inner heat sealable ply is capable of forming a heat seal with itself as well as with the septum retainer 16.

The barrier layer is a material or structure such as a film, layer, membrane or surface coating which prevents or reduces the penetration or permeation of vapors or gases through or beyond the barrier. The barrier layer in accordance with the present invention may be constructed of a metallic foil or a high barrier polymer although other types of barriers may also be useful.

Preferably, the high barrier polymer forms a film having a moisture vapor transmission rate (MVTR) no greater than about 0.065 g/100 in.$^2$/24 hrs @100° F.,90% RH. More preferably, the barrier film has an MVTR substantially competitive with that of a film of aluminum foil of between about 0.02 to 0.04 g/100 in.$^2$/24 hrs @100° F.,90% RH. Suitable materials for the barrier layer include, but are not limited to, silane materials, such as a SiOx coating and modified fluoropolymer films such as polychlorotrifluoroethylene (PCTFE) films. One example of a PCTFE material useful as a barrier layer is available commercially under the trade name ACLAR®, manufactured by Honeywell. This material is particularly useful as it is transparent, allowing for the visual inspection of the fill volume during the fill process to determine if it is correct and visual inspection of the seal to determine if it is intact.

As shown in FIG. 3, the needle guide 14 is secured to the outer face 24 of the packet 12 and the septum retainer 16 is secured to the inner face 26 of the packet 12 in substantial alignment with the needle guide 14. In accordance with a particular aspect of the present invention, the needle guide 14 is secured to the outer face 24 of the packet 12 using a UV cured liquid adhesive (not shown). The UV cured liquid adhesive used to secure the needle guide 14 to the outer face 24 of the packet 12 can be any material that exhibits the desired adhesion between the two materials. While a UV cured liquid adhesive is used in accordance with particular embodiments of the invention, double sided acrylic tape can also be used in some applications. Furthermore, the needle guide 14 could be secured to the outer face 24 of the packet 12 using other known methods such as heat-sealing, ultrasonic welding, etc.

The septum retainer 16 is preferably secured to the inner face 26 of the packet 12 by heat-sealing to minimize the potential for contamination from conventional securing means such as using an adhesive coating. This is particularly important when the liquid contents are pharmaceutical agents. It is also important in particular embodiments of the present invention that the fluid contacting layer of the multi-ply film contain no plasticizer which may contaminate the fluid contents of the container. Again, this may not be required for all liquids but is considered important when the liquid is a pharmaceutical agent. To form a heat seal between the septum retainer 16 and the inner face 26 of the packet 12, the septum retainer 16 and inner face 26 preferably comprise compatible materials that form a suitable heat-seal.

In accordance with certain embodiments, the septum retainer 16 and the inner face 26 of the packet 12 are compatible polyester materials, such as polyethylene terephthalate (PET). Other compatible materials that could be used include, but are not limited to, other thermoplastic materials, such as other polyesters, polyethylene (low density (LDPE), linear low density (LLDPE), high density (HDPE)), polypropylene, acrylonitrile, polyamide, polyvinylidinefluoride (PVDF), ethylene acrylic acid, ethylene/methacrylic acid (E/MAA) copolymer, polypropylene lacquer, polyacetal and copolymers thereof. In other applications subject to less stringent requirements, the septum retainer 16 can be secured to the inner face 26 of the packet 12 using any conventional means such as tape, adhesive film coating, welding, etc.

Figure 4:
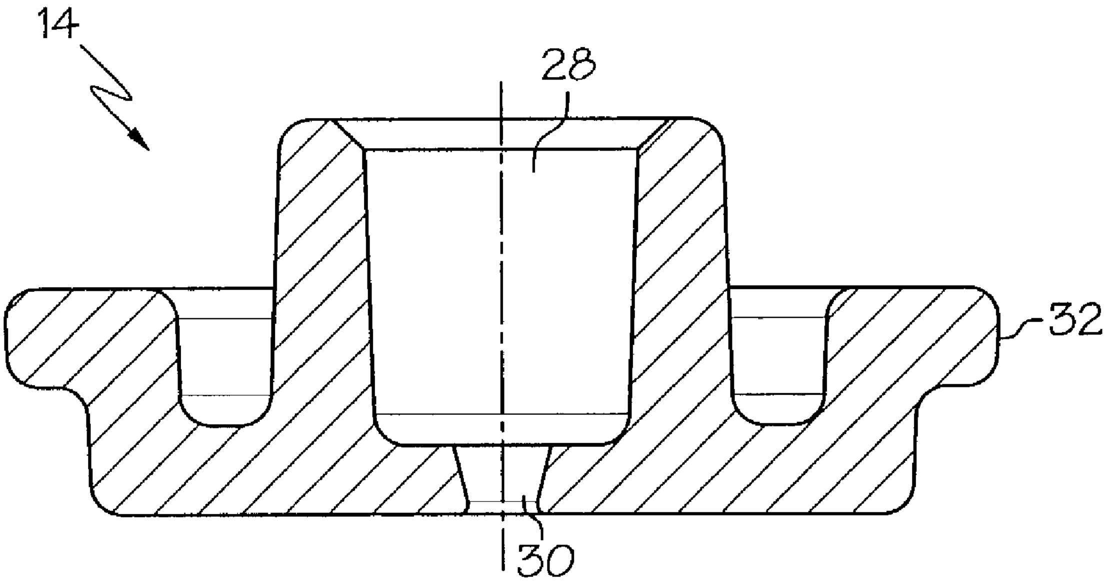
FIG. 4 is an enlarged cross-section of a needle guide in accordance with one embodiment of the invention.

The needle guide 14 is shown in greater detail in FIG. 4. In accordance with the embodiment as shown in FIG. 4, the needle guide 14 includes a centrally located cylindrical tube 28 for receiving a needle and insuring proper alignment of the needle. Cylindrical tube 28 leads to a narrow aperture 30 which provides further alignment of the needle. Cylindrical tube 28 and aperture 30 may include beveled edges to facilitate insertion and alignment of the needle.

In some applications it may be desirable to provide a mechanism for holding the collapsible sealed packet after it is pierced with a needle in such a way that there is only minimal pressure exerted on the packet and its contents. Pressure on the package may be a concern because it could force liquid into the needle thereby interfering with the controlled delivery of the liquid to the liquid delivery device. In accordance with one embodiment, the needle guide 14 further comprises a radially outwardly extending annular flange 32 wherein the annular flange allows the packet to be securely held without applying pressure to the packet itself. In accordance with this embodiment, the liquid delivery device may include a two pronged fork which engages the annular flange 32 drawing the packet 12 into alignment with the needle. Once the container is in position in the liquid delivery device, it can be pierced with the needle thereby providing secure positioning between the packet 12 and the liquid delivery device during fluid delivery.

In accordance with another embodiment, the packet 12 may be retained in a small tray or cartridge holder that can be inserted into a fluid delivery device such that the needle guide 14 is in alignment with the needle. The tray or cartridge may include a slot having a wide end and a narrow end. The packet 12 may be disposed inside the tray or cartridge with the annular flange 32 extending through the slot in the holder. The annular flange initially extends through the wide end of the slot and is then moved laterally to position the annular flange 32 in the narrow end of the slot to securely seat the packet 12 in the holder. Those skilled in the art will appreciate that other methods are available for securing the packet 12 to the liquid delivery device.

Figure 5:
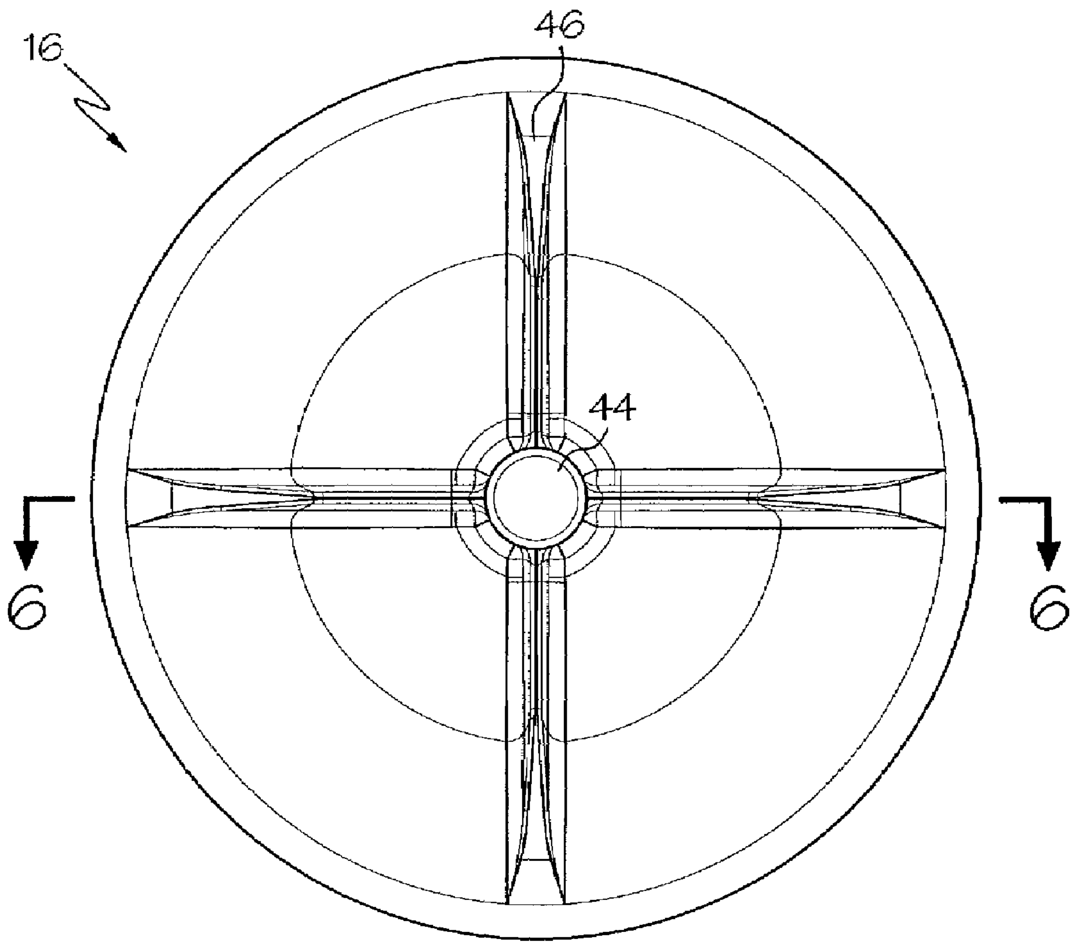
FIG. 5 is a bottom view of a septum retainer in accordance with one embodiment of the present invention.
Figure 6:
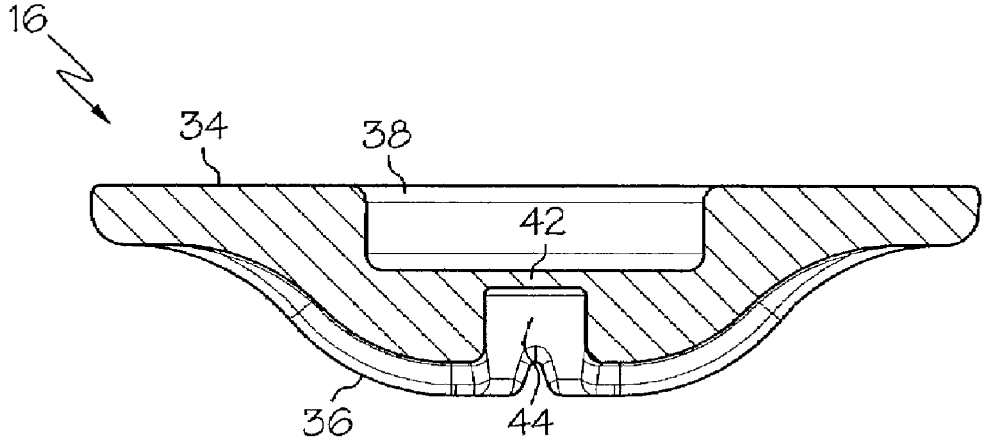
FIG. 6 is a cross-section of the septum retainer of FIG. 5 along the line 6—6.

FIGS. 5 and 6 illustrate a septum retainer 16 in accordance with one embodiment of the present invention. Septum retainer 16 in accordance with this embodiment is generally circular in shape with a base portion 34 and a raised dome portion 36. A centrally located septum chamber 38 is provided in base portion 34. The septum chamber 38 may include a septum barrier 42 which enables septum 40 to be retained in isolation from the liquid contents of the packet. Retaining the septum 40 in isolation from the liquid contents of the package refers to minimizing the potential for contamination of the liquid contents with leachates from the septum. Various methods may be employed to accomplish the isolation of the septum from the contents of the packet. The septum barrier 42 provides a physical barrier and prevents the septum 40 from being exposed to the liquid contents of the packet until the product is ready for use at which time the septum barrier 42 is pierced by the needle as the liquid delivery process is initiated. Chemical barriers can also be employed to increase the isolation of the septum from the contents of the packet. The septum retainer 16, septum 40 or both can be coated with a barrier coating to provide additional isolation of the septum from the liquid contents of the packet. The barrier coating, when used, prevents or greatly reduces silicone plasticizers from leaching out of the septum 16 and potentially contaminating the liquid contents of the packet. Particularly useful barrier coatings are available commercially from Specialty Coating Systems under the trade name Parylene®. These materials are conformable coatings deposited from the vapor phase. The polymers include poly-p-xylylene and derivatives thereof.

Septum retainer 16 further comprises a cavity 44 coaxial with the septum chamber 38. The cavity 44 receives the tip of an inserted needle and prevents the tip from contacting the adjacent face of the packet.

In accordance with the illustrated embodiment of the invention, the septum retainer 16 further comprises a plurality of channels 46 extending radially from the cavity 44 to the circumferential edge of the base 34. Channels 46 in combination with the raised dome portion 36 of the septum retainer 16 prevent premature collapse of the packet in the vicinity of cavity 44 thereby allowing almost complete withdrawal of liquid from the packet 12.

As best shown in FIG. 3, the needle guide 14 on the outer face 24 of the packet 12 is aligned with the septum retainer 16 on the inner face 26. The needle guide 14 and septum retainer 16 may include complementary contours which facilitate alignment of the septum retainer with the needle guide when the septum retainer is placed on the inner face 26 of the packet 12 and the needle guide 14 is placed on the outer face 24 of the packet 12. When properly aligned, the cylindrical tube 28 and aperture 30 of the needle guide 14 are coaxial with the septum chamber 38 and cavity 44 of the septum retainer 16. In use, a needle in fluid communication with a liquid delivery device is inserted through the cylindrical tube 28 and the aperture 30 of the needle guide such that the tip of the needle pierces the packet 12. The tip of the needle is inserted through the septum 40 and pierces septum barrier 42 so as to establish fluid communication between the liquid delivery device and the contents of the packet 12. The tip of the inserted needle resides in the cavity 44 thereby preventing the tip from contacting the adjacent face of the packet 12. As liquid is withdrawn from the packet 12, the packet collapses but fluid delivery continues as the liquid travels along channels 46 to cavity 44 in the raised dome portion 36 of the septum retainer 16.

The cavity 44 in the septum retainer 16 functions as a sump in its location in septum chamber 38 adjacent inner face 26 of the packet 12. Any air in the container is maintained above the needle and, therefore, liquid can be withdrawn from the packet 12 free of air. The septum 40 preferably is thick enough to prevent leakage around the needle. A thickness of approximately 0.04 inch is typically sufficient for this purpose. The septum 40 typically is constructed of elastomeric materials, such as natural and silicone rubber, as well as other thermoplastic elastomers. One specific example of a useful material is ethylene propylene diene monomer (EPDM). Other useful materials are known to those of skill in the art.

The liquid containment system of the present invention is particularly useful for the storage of a medicament dissolved in a solvent or liquid carrier vehicle, for producing an aerosol for inhalation therapy. Solvents typically used include water, ethanol or mixtures thereof. A co-solvent may be used in the liquid carrier vehicle for example mono- and polyvalent alcohols such as propylene glycol, glycerol, and polyethylene glycol (PEG) having an average molecular weight between about 200 and 4000, preferably between about 200 and 400.

Pharmaceutically active agents dissolved in ethanol or other alcohols may cause leaching or degradation of adhesives that come in contact with the liquid contained in the packet 12. Accordingly, heat-sealing is particularly preferred in those applications wherein the packet 12 contains an alcohol based liquid. By contrast, water based solutions are less likely to cause leaching or degradation of adhesives and, therefore, the use of adhesives to seal the packet or adhere the septum retainer to the inner face 26 of the packet 12 may be acceptable. The liquid contents of the packet 12 may be solutions, suspensions, or emulsions.

The term "pharmaceutically active agent" refers to biologically active agents that are used for diagnostic purposes as well as agents that are administered to human or animal patients as the active drug substance for treatment of a disease or condition. Such active drug substances are administered to a patient in a "pharmaceutically effective amount" to treat a disease or condition. As would be recognized by one skilled in the art, by "effective amount" is meant an amount of a pharmaceutically active agent having a therapeutically relevant effect on the disease or condition to be treated. A therapeutically relevant effect relieves to some extent one or more symptoms of the disease or condition in a patient or returns to normal either partially or completely one or more physiological or biochemical parameters associated with or causative of the disease or condition. Specific details of the dosage of a particular active drug may be found in its labeling, i.e., the package insert (see 21 CFR § 201.56 & 201.57) approved by the United States Food and Drug Administration.

The type of pharmaceutically active agents that may be used with the present invention are not particularly limited. Examples include those which are listed within the Physician's Desk Reference (most recent edition). The device is particularly useful in the administration of drugs for the treatment of respiratory diseases and in particular the treatment of diseases such as asthma, bronchitis, emphysema and cystic fibrosis. Such drugs include beta adrenergic agonists which include bronchodilators including albuterol, isoproterenol sulfate, metaproterenol sulfate, terbutaline sulfate, pirbuterol acetate, salmeterol xinotoate, formoteorol; steroids including corticosteroids used as an adjunct to beta agonist bronchodilators such as beclomethasone dipropionate, flunisolide, fluticasone, budesonide and triamcinolone acetonide; antibiotics including antifungal and antibacterial agents such as chloramphenicol, chlortetracycline, ciprofloxacin, framycetin, fusidic acid, gentamicin, neomycin, norfloxacin, ofloxacin, polymyxin, propamidine, tetracycline, tobramycin, quinolines, and the like; and also includes peptide nonadrenergic noncholinergic neurotransmitters and anticholinergics. Antiinflammatory drugs used in connection with the treatment of respiratory diseases include steroids such as beclomethasone dipropionate, triamcinolone acetonide, flunisolide and fluticasone. Other antiinflammatory drugs and antiasthmatics which include cromoglycates such as cromolyn sodium. Other respiratory drugs which would qualify as bronchodilators include anticholinergics including ipratropium bromide. Other useful respiratory drugs include leukotriene (LT) inhibitors, vasoactive intestinal peptide (VIP), tachykinin antagonists, bradykinin antagonists, endothelin antagonists, heparin furosemide, antiadhesion molecules, cytokine modulators, biologically active endonucleases, recombinant human (rh) DNase, antitrypsin and antibiotics such as gentamicin, tobramycin, cephalosporins or penicillins, nucleic acids and gene vectors.

The present invention is intended to encompass the free acids, free bases, salts, amines and various hydrate forms including semihydrate forms of such respiratory drugs and is particularly directed towards pharmaceutically acceptable formulations of such drugs which are formulated in combination with pharmaceutically acceptable excipient materials generally known to those skilled in the art. Pharmaceutically acceptable excipients are those recognized by the FDA as being safe for use in humans. Additives such as, antioxidants, e.g., Vitamin E, Vitamin E TPGS (α—alpha tocopferol polyethylene glycol 1000 succinate), ascorbic acid, anti-microbials, e.g, parabens, pH adjusting agents, e.g., sodium hydroxide and hydrochloric acid, tonicity adjusting agents, e.g., sodium chloride and viscosity adjusting agents, e.g., polyvinyl pyrrolidone are contemplated for use herein. While the selection of any particular pharmaceutically acceptable excipient is within the skill of the art, the decision regarding whether to add an excipient and if so which one, will be made taking into account the purpose of the excipient in a specific liquid carrier vehicle. In order to be pharmaceutically acceptable any formulation excipient used in the carrier liquids of the invention should be recognized by the FDA as safe for use in humans. Additionally, an excipient should have no effect or minimal effect on the sprayability of formulations of a drug dissolved or suspended in a liquid carrier using an electrohydrodynamic (EHD) spraying means.

In accordance with certain aspects of the present invention the formulations consist essentially of pharmaceutically active drug and a pharmaceutically acceptable carrier (e.g., water and/or ethanol). However, if a drug is liquid without an excipient the formulation may consist essentially of the drug provided that it has a sufficiently low viscosity that it can be aerosolized using a dispenser with the present invention.

In accordance with one embodiment of the present invention, the liquid containment system as described herein is particularly useful for containing solutions or suspensions of a medicament for delivery to a delivery device. In accordance with a specific embodiment of the invention, the delivery device may be a micropump which supplies metered amounts of the liquid in predetermined doses to an aerosol sprayer. More particularly, the containment system is useful in containing doses of a medicament for delivery to a micropump as disclosed in commonly assigned U.S. patent application Ser. No. 10/187,423, now U.S. Pat. No. 6,827,559, entitled "Piezoelectric Micropump with Diaphragm and Valves" for use with EHD aerosol sprayers such as the type disclosed in U.S. Pat. No. 6,302,331 to Dvorsky et al.

Having described the invention in detail by reference to specific embodiments thereof, it will be apparent that numerous modifications and variations are possible without departing from the spirit and scope of the following claims:

What is claimed is:

1. A container closure device for facilitating withdrawal a liquid from a collapsible sealed packed comprising:

a needle guide and a septum retainer, the needle guide fixed to an outer face of a sealed packet and the septum retainer fixed to an inner face of the sealed packet in alignment with the needle guide, the needle guide including a tube for receiving a needle and insuring proper alignment of the needle, and the septum retainer having a septum and a plurality of channels disposed therein and a raised portion having a cavity formed therein for inhibiting collapse of the packet into the cavity, the cavity for receiving a tip of an inserted needle wherein the channels allow for contained liquid withdrawal as the packet collapses.

2. The container closure device of claim 1 wherein the septum retainer and inner face of the packet are constructed of materials capable of forming a heat seal to secure the septum retainer to the inner face of the packet.

3. The container closure device of claim 2 wherein each of the septum retainer and the inner face of the packet comprises at least one material selected from the group consisting of polyester, polyamide, polyethylene, polypropylene, polyvinylidine fluoride, ethylene acrylic acid, ethylene/methacrylic acid copolymer, acrylonitrile, polyacetal, and mixtures and copolymers thereof.

4. The container closure device of claim 3 wherein each of the septum retainer and inner face of the packet comprises polyethylene terephthalate or acrylonitrile.

5. The container closure device of claim 1 wherein the needle guide further comprises a radially outwardly extending annular flange on the needle guide.

6. The container disclosure device of claim 5 wherein the annular flange allows the packet to be securely held without applying pressure to the packet itself.

7. The container closure device of claim 1 wherein the septum retainer cavity further is adapted to prevent the tip from contacting the adjacent face of the packet.

8. The container closure device of claim 1 wherein the septum retainer further comprises a chamber wherein the septum is retained in isolation from the liquid contents of the packet.

9. The container closure device of claim 1 wherein the needle guide and the septum retainer include complementary contours thereby facilitating alignment of the septum retainer with the needle guide when the septum retainer is placed on the inner face of the packet and the needle guide is placed on the outer face of the packet.

10. The container closure device of claim 1 wherein the septum retainer cavity is adapted to provide a sump from which said liquid can be withdrawn without entraining residual air.

11. The container closure device of claim 1 wherein said packet contains a liquid comprising a pharmaceutically active material.

12. A liquid containment system comprising a collapsible sealed packet, a needle guide and a septum retainer, the collapsible sealed packet comprising first and second flexible sheets superimposed and sealed together at their periphery to form a packet defining an interior for containing a liquid, the needle guide secured to an outer face of the packet, and the septum retainer secured to an inner face of the packet in alignment with the needle guide, the septum retainer including a raised portion having formed therein a cavity for inhibiting collapse of the packet into the cavity and for receiving a tip of an inserted needle, said septum retainer further comprising a plurality of channels which allow for contained liquid withdrawal as the packet collapses.

13. The liquid containment system of claim 12 wherein each of said first and second flexible sheets is a multilayer film comprising:

a barrier layer comprising a barrier material selected from the group consisting of foils and barrier polymers; and an inner layer comprising a material selected from the group consisting of acrylonitrile and polyester;

wherein said inner layer is positioned between said interior of said packet and said barrier layer.

14. The liquid containment system of claim 13 wherein said multilayer film further comprises an outer layer comprising polyester;

wherein said barrier layer is positioned between said outer layer and said inner layer.

15. The liquid containment system of claim 14 wherein said inner layer comprises polyethylene terephthalate and said outer layer comprises polyethylene terephthalate.

16. The liquid containment system of claim 15 wherein the septum retainer comprises a polyethylene terephthalate and a heat-seal is formed between the inner layer and the septum retainer to secure the septum retainer to the inner face of the packet.

17. The liquid containment systems of claim 12 wherein said liquid comprises a pharmaceutically active material.

18. The liquid containment system of claim 12 wherein said needle guide includes a tube for receiving a needle and insuring proper alignment of the needle, and the septum retainer comprises a chamber wherein a septum is retained in isolation from the liquid contents of the packet.

19. The liquid containment system of claim 12 wherein the septum retainer cavity is adapted to prevent the tip from contacting the adjacent face of the packet; and to provide a sump from which said liquid can be withdrawn without entraining residual air.

20. The liquid containment system of claim 12 wherein said needle guide comprises a radially outwardly extending annular flange wherein the annular flange enables the packet to be securely held without applying pressure to the packet itself.

21. A device comprising:

a collapsible sealed packet; and a septum retainer fixed to an inner face of the sealed packet, said septum retainer having a raised portion having a cavity formed therein for inhibiting collapse of the packet into the cavity, the cavity for receiving a tip of a needle inserted into the sealed packet, said septum retainer further comprising a plurality of channels which allow for contained liquid withdrawal as the packet collapses.

22. The container closure device of claim 21 wherein the septum retainer cavity further is adapted to prevent the tip from contacting the adjacent face of the packet.

23. The container closure device of claim 21 wherein the septum retainer cavity provides a sump from which said liquid can be withdrawn without entraining residual air.

24. A liquid containment system comprising:

a collapsible sealed packet comprising first and second flexible sheets superimposed and sealed together to form a packet defining an interior for containing a liquid, and a septum retainer secured to an inner face of the packet, the septum retainer including a raised portion having formed therein a cavity for inhibiting collapse of the packet into the cavity and a plurality of channels which allow for continued liquid withdrawal as the packet collapses, the cavity for receiving a tip of a needle inserted into said packet.

25. The liquid containment systems of claim 24 wherein said liquid comprises a pharmaceutically active material.

26. The liquid containment system of claim 24 wherein the septum retainer cavity is adapted to prevent the tip from contacting the adjacent face of the packet and to provide a sump from which said liquid can be withdrawn without entraining residual air.

* * * * *